(12) United States Patent
Rosenthal et al.

(10) Patent No.: US 9,650,627 B1
(45) Date of Patent: May 16, 2017

(54) SITE-DIRECTED RNA EDITING

(71) Applicants: Joshua J. C. Rosenthal, Vega Alta, PR (US); Maria Fernanda Montiel-Gonzalez, San Juan, PR (US)

(72) Inventors: Joshua J. C. Rosenthal, Vega Alta, PR (US); Maria Fernanda Montiel-Gonzalez, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 213 days.

(21) Appl. No.: 13/947,027

(22) Filed: Jul. 20, 2013

Related U.S. Application Data

(60) Provisional application No. 61/673,497, filed on Jul. 19, 2012.

(51) Int. Cl.
  *C12N 15/11*  (2006.01)
  *C12N 15/10*  (2006.01)
(52) U.S. Cl.
  CPC ............................. *C12N 15/1024* (2013.01)

(58) Field of Classification Search
  CPC ..................... C12N 15/113; C12N 2310/11
  See application file for complete search history.

(56) References Cited

PUBLICATIONS

Kwak et al. J. Mol. Med. 2005, 83: 110-120.*

* cited by examiner

*Primary Examiner* — Brian Whiteman
(74) *Attorney, Agent, or Firm* — Hoglund & Pamias, PSC; Roberto J. Rios (57) ABSTRACT

The invention provides a way to target RNA editing by adenosine deamination to a chosen adenosine within RNA. An antisense RNA oligonucleotide is used for targeting the entire complex to a specific address on the RNA molecule. A Box B RNA and a λ N-peptide are used as a linkage between the antisense RNA oligonucleotide and a deaminase domain of human ADAR2 used to catalyze the deamination of the specific adenosine residue. These elements make up two molecules: the antisense RNA Oligo Box B RNA hairpin forms a single unit, as does the λ N-peptide-deaminase domain of human ADAR2.

5 Claims, 3 Drawing Sheets

SEQUENCE LISTING

```
<160> NUMBER OF SEQ ID NOS: 8

<210> SEQ ID NO 1
<211> LENGTH: 405
<212> TYPE: PRT
<213> ORGANISM: Homo Sapiens

<400> SEQUENCE: 1

Leu His Leu Asp Gln Thr Pro Ser Arg Gln Pro Ile Pro Ser Glu Gly
1               5                   10                  15

Leu Gln Leu His Leu Pro Gln Val Leu Ala Asp Ala Val Ser Arg Leu
            20                  25                  30

Val Leu Gly Lys Phe Gly Asp Leu Thr Asp Asn Phe Ser Ser Pro His
        35                  40                  45

Ala Arg Arg Lys Val Leu Ala Gly Val Val Met Thr Thr Gly Thr Asp
    50                  55                  60

Val Lys Asp Ala Lys Val Ile Ser Val Ser Thr Gly Thr Lys Cys Ile
65                  70                  75                  80

Asn Gly Glu Tyr Met Ser Asp Arg Gly Leu Ala Leu Asn Asp Cys His
                85                  90                  95

Ala Glu Ile Ile Ser Arg Arg Ser Leu Leu Arg Phe Leu Tyr Thr Gln
            100                 105                 110

Leu Glu Leu Tyr Leu Asn Asn Lys Asp Asp Gln Lys Arg Ser Ile Phe
        115                 120                 125

Gln Lys Ser Glu Arg Gly Gly Phe Arg Leu Lys Glu Asn Val Gln Phe
    130                 135                 140

His Leu Tyr Ile Ser Thr Ser Pro Cys Gly Asp Ala Arg Ile Phe Ser
145                 150                 155                 160

Pro His Glu Pro Ile Leu Glu Glu Pro Ala Asp Arg His Pro Asn Arg
                165                 170                 175

Lys Ala Arg Gly Gln Leu Arg Thr Lys Ile Glu Ser Gly Glu Gly Thr
            180                 185                 190
```

```
Ile Pro Val Arg Ser Asn Ala Ser Ile Gln Thr Trp Asp Gly Val Leu
            195                 200                 205

Gln Gly Glu Arg Leu Leu Thr Met Ser Cys Ser Asp Lys Ile Ala Arg
        210                 215                 220

Trp Asn Val Val Gly Ile Gln Gly Ser Leu Leu Ser Ile Phe Val Glu
225                 230                 235                 240

Pro Ile Tyr Phe Ser Ile Ile Leu Gly Ser Leu Tyr His Gly Asp
                245                 250                 255

His Leu Ser Arg Ala Met Tyr Gln Arg Ile Ser Asn Ile Glu Asp Leu
            260                 265                 270

Pro Pro Leu Tyr Thr Leu Asn Lys Pro Leu Leu Ser Gly Ile Ser Asn
        275                 280                 285

Ala Glu Ala Arg Gln Pro Gly Lys Ala Pro Asn Phe Ser Val Asn Trp
    290                 295                 300

Thr Val Gly Asp Ser Ala Ile Glu Val Ile Asn Ala Thr Thr Gly Lys
305                 310                 315                 320

Asp Glu Leu Gly Arg Ala Ser Arg Leu Cys Lys His Ala Leu Tyr Cys
                325                 330                 335

Arg Trp Met Arg Val His Gly Lys Val Pro Ser His Leu Leu Arg Ser
            340                 345                 350

Lys Ile Thr Lys Pro Asn Val Tyr His Glu Ser Lys Leu Ala Ala Lys
        355                 360                 365

Glu Tyr Gln Ala Ala Lys Ala Arg Leu Phe Thr Ala Phe Ile Lys Ala
    370                 375                 380

Gly Leu Gly Ala Trp Val Glu Lys Pro Thr Glu Gln Asp Gln Phe Ser
385                 390                 395                 400

Leu Thr Pro Leu Val
                405

<210> SEQ ID NO 2
<211> LENGTH: 17
<212> TYPE: RNA
<213> ORGANISM: Homo Sapiens

<400> SEQUENCE: 2
ggcccugaaa aagggcc                                                   17

<210> SEQ ID NO 3
<211> LENGTH: 21
<212> TYPE: PRT
<213> ORGANISM: Homo Sapiens

<400> SEQUENCE: 3

Asn Ala Arg Thr Arg Arg Glu Arg Arg Ala Glu Lys Gln Ala Gln
1               5                   10                  15

Trp Lys Ala Ala Asn
            20

<210> SEQ ID NO 4
<211> LENGTH: 1575
<212> TYPE: DNA
<213> ORGANISM: doryteuthis opalescens

<400> SEQUENCE: 4
atggtggtgg gtaaaaaatc aaaaaaagaa aagctgatta tgacaaatat aggaggaggt    60
ggtggagatg agaaggggc ccctgttgga gactgtacag accccaacca gacatgcgtt    120
gttaacaatt ctcactgtga ttctaacctt gccaattcca ggtcatttcc caaacacaca   180
```

```
gaggacgaca atgtccatgt cgaggatgga atgggtccgg gcagtgacta tgaacggtgt      240
gagcgcgtcg ttatcaacgt gagcggcctc cggttcgaaa cccaactcag gacccttgct      300
cagtttcctg acacgttact cggcaaccct aaaaaaagga atcgctatta cgacccgttg      360
cggaatgaat atttttttga tcgaaatcgt cccagctttg acgcaattct ctattactac      420
cagagtggcg gccggttgag aaaacctgtc aacgtaccac tggacgtgtt ctccgaggag      480
atcaagttct acgaactggg tgctgaagcc atagaaaaat accgcgacga tgaaggtttt      540 attaagaag aggaccgacc tcttcctgaa aatgagttcc agcgacgagt ctggttactc       600
ttcgaatatc cggagagttc aacagccgct cgtctcatag ctattttttc tgtggtgatt      660
attctacttt ccattgtgat attctgcctt gagaccctgc ccgagttcaa gcactaccga      720
ttggtgaatg agacaattga ggaagacgac ataccaaaat ttggagaacc tttcttcatt      780
atagaaacct gctgcataat atggttcacg tccgaactga tggtaagatt tgcttcttgc      840
cctgaaaaaa taggtttctt caagaacatc atgaatctta ttgacattgt tgccattatt      900
ccatatttca tcaccttggg aaccgttatc gctgacgaaa acaaaagcaa caaccaagcg      960
atgtcgcttg cgattcttag ggtcattcga ttagttagag ttttccgtat tttcaagctc      1020
tctagacatt ctaaaggatt acaaatactc ggccagaccc tcaaagccag catgagggaa      1080
ctcggtcttt taatattctt cttatttatt ggagtgatct tattctctag tgctgtatac      1140
ttcgcagaag ccgatgctga acagacacat ttcaaaagca tacctgacgc ttttggtgg      1200 gccgtggtta ctatgactac ggtaggttac ggggacatga ggcccattgg ggtctggggc      1260
aagttggtcg ggtcactatg tgccattgca ggtgtgttga cgatcgcatt acccgtaccg      1320
gtcattgttt ccaactttaa ctattttat cacagagaga cagaaagtga cgataaggat       1380
aagtaccatc acgtcacgtc ggccataaac tatccggaaa acgtagttc gtatgtgtcg       1440 gagaatggct ccgacataat ggagatggag gagggcagtg tgattaatga acggataaaa      1500
gaaaaccatg ccgttaaggt gaacaacccg accaacatta tatgaataa cttaagtata       1560 gagactgacg tttga                                                       1575
```

<210> SEQ ID NO 5
<211> LENGTH: 4443
<212> TYPE: DNA
<213> ORGANISM: Homo Sapiens

<400> SEQUENCE: 5

```
atgcagaggt cgcctctgga aaaggccagc gttgtctcca aactttttt cagctggacc         60 agaccaattt tgaggaaagg atacagacag cgcctggaat tgtcagacat ataccaaatc       120
ccttctgttg attctgctga caatctatct gaaaaattgg aaagagaatg ggatagagag       180
ctggcttcaa agaaaaatcc taaactcatt aatgcccttc ggcgatgttt ttctggaga        240 tttatgttct atggaatctt tttatattta ggggaagtca ccaaagcagt acagcctctc       300
ttactgggaa gaatcatagc ttcctatgac ccggataaca aggaggaacg ctctatcgcg       360
atttatctag gcataggctt atgccttctc tttattgtga ggacactgct cctacaccca       420
gccatttttg gccttcatca cattggaatg cagatgagaa tagctatgtt tagtttgatt       480
tataagaaga ctttaaagct gtcaagccgt gttctagata aaataagtat tggacaactt      540
gttagtctcc tttccaacaa cctgaacaaa tttgatgaag acttgcatt ggcacatttc        600 gtgtggatcg ctccctttgca agtggcactc ctcatggggc taatctggga gttgttacag     660
```

```
gcgtctgcct tctgtggact tggtttcctg atagtccttg ccctttttca ggctgggcta    720
gggagaatga tgatgaagta cagagatcag agagctggga agatcagtga aagacttgtg    780
attacctcag aaatgattga aaatatccaa tctgttaagg catactgctg ggaagaagca    840
atggaaaaaa tgattgaaaa cttaagacaa acagaactga aactgactcg gaaggcagcc    900
tatgtgagat acttcaatag ctcagccttc ttcttctcag ggttctttgt ggtgttttta    960
tctgtgcttc cctatgcact aatcaaagga atcatcctcc ggaaaatatt caccaccatc   1020
tcattctgca ttgttctgcg catggcggtc actcggcaat tccctgggc tgtacaaaca    1080 tggtatgact ctcttggagc aataaacaaa atacaggatt tcttacaaaa gcaagaatat   1140
aagacattgg aatataactt aacgactaca gaagtagtga tggagaatgt aacagccttc   1200
tgggaggagg gatttgggga attatttgag aaagcaaaac aaaacaataa caatagaaaa   1260
acttctaatg gtgatgacag cctcttcttc agtaatttct cacttcttgg tactcctgtc   1320
ctgaaagata ttaatttcaa gatagaaaga ggacagttgt tggcggttgc tggatccact   1380
ggagcaggca agacttcact tctaatggtg attatgggag aactggagcc ttcagagggt   1440
aaaattaagc acagtggaag aatttcattc tgttctcagt tttcctagat tatgcctggc   1500
accattaaag aaaatatcat ctttggtgtt tcctatgatg aatatagata cagaagcgtc   1560
atcaaagcat gccaactaga agaggacatc tccaagtttg cagagaaaga caatatagtt   1620
cttggagaag gtggaatcac actgagtgga ggtcaacgag caagaatttc tttagcaaga   1680
gcagtataca agatgctga tttgtattta ttagactctc cttttggata cctagatgtt   1740
ttaacagaaa agaaatatt tgaaagctgt gtctgtaaac tgatggctaa caaaactagg   1800
attttggtca cttctaaaat ggaacattta agaaagctg acaaaatatt aattttgcat   1860
gaaggtagca gctattttta tgggacattt tcagaactcc aaaatctaca gccagctttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa acaatctttt taaacagact ggagagtttg gggaaaaaag gaagaattct   2100
attctcaatc caatcaactc tatacgaaaa ttttccattg tgcaaaagac tcccttacaa   2160
atgaatggca tcgaagagga ttctgatgag cctttagaga aaggctgtc cttagtacca   2220 gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacataccct cgatatatta ctgtccacaa gagcttaatt   2580
tttgtgctaa tttggtgctt agtaattttt ctggcagagg tggctgcttc tttggttgtg   2640
ctgtggctcc ttgaaacac tcctcttcaa gacaaaggga atagtactca tagtagaaat   2700
aacagctatg cagtgattat caccagcacc agttcgtatt atgtgttta catttacgtg   2760 ggagtagccg acactttgct tgctatggga ttcttcagag tctaccact ggtgcatact   2820 ctaatcacag tgtcgaaaat tttacaccac aaaatgttac attctgttct tcaagcacct   2880
atgtcaaccc tcaacacgtt gaaagcaggt gggattctta atagattctc caaagatata   2940
gcaattttgg atgaccttct gcctcttacc atatttgact tcatccagtt gttattaatt   3000
gtgattggag ctatagcagt tgtcgcagtt ttacaaccct acatctttgt tgcaacagtg   3060
```

```
ccagtgatag tggctttat tatgttgaga gcatatttcc tccaaacctc acagcaactc    3120
aaacaactgg aatctgaagg caggagtcca attttcactc atcttgttac aagcttaaaa    3180
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttatttttc tggaacattt    3900 agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagcccccga ttgctgctct gaaagaggag acagaagaag aggtgcaaga tacaaggctt    4440
tag                                                                 4443
```

<210> SEQ ID NO 6
<211> LENGTH: 8886
<212> TYPE: DNA
<213> ORGANISM: Homo Sapiens

<400> SEQUENCE: 6

```
atgcagaggt cgcctctgga aaaggccagc gttgtctcca aactttttt cagctggacc     60 agaccaattt tgaggaaagg atacagacag cgcctggaat tgtcagacat ataccaaatc    120
ccttctgttg attctgctga caatctatct gaaaaattgg aaagagaatg ggatagagag    180
ctggcttcaa agaaaaatcc taaactcatt aatgcccttc ggcgatgttt tttctggaga    240
tttatgttct atggaatctt tttatattta ggggaagtca ccaaagcagt acagcctctc    300
ttactgggaa gaatcatagc ttcctatgac ccggataaca aggaggaacg ctctatcgcg    360
atttatctag gcataggctt atgccttctc tttattgtga ggacactgct cctacaccca    420 gccattttg gccttcatca cattggaatg cagatgagaa tagctatgtt tagtttgatt    480
tataagaaga ctttaaagct gtcaagccgt gttctagata aaataagtat tggacaactt    540
gttagtctcc tttccaacaa cctgaacaaa tttgatgaag acttgcatt ggcacatttc    600 gtgtggatcg ctccctttgca agtggcactc ctcatggggc taatctggga gttgttacag    660
```

```
gcgtctgcct tctgtggact tggtttcctg atagtccttg cccttttttca ggctgggcta    720
gggagaatga tgatgaagta cagagatcag agagctggga agatcagtga aagacttgtg    780
attacctcag aaatgattga aaatatccaa tctgttaagg catactgctg ggaagaagca    840
atggaaaaaa tgattgaaaa cttaagacaa acagaactga aactgactcg gaaggcagcc    900
tatgtgagat acttcaatag ctcagccttc ttcttctcag ggttcttttgt ggtgttttta    960
tctgtgcttc cctatgcact aatcaaagga atcatcctcc ggaaaatatt caccaccatc   1020
tcattctgca ttgttctgcg catggcggtc actcggcaat tccctgggc tgtacaaaca   1080
tggtatgact ctcttggagc aataaacaaa atacaggatt tcttacaaaa gcaagaatat   1140
aagacattgg aatataactt aacgactaca gaagtagtga tggagaatgt aacagccttc   1200
tgggaggagg gatttgggga attatttgag aaagcaaaac aaaacaataa caatagaaaa   1260
acttctaatg gtgatgacag cctcttcttc agtaatttct cacttcttgg tactcctgtc   1320
ctgaaagata ttaatttcaa gatagaaaga ggacagttgt tggcggttgc tggatccact   1380
ggagcaggca agacttcact tctaatggtg attatgggag aactggagcc ttcagagggt   1440
aaaattaagc acagtggaag aatttcattc tgttctcagt tttcctggat tatgcctggc   1500
accattaaag aaaatatcat ctttggtgtt tcctatgatg aatatagata cagaagcgtc   1560
atcaaagcat gccaactaga agaggacatc tccaagtttg cagagaaaga caatatagtt   1620
cttggagaag gtgaatcac actgagtgga ggtcaacgag caagaatttc tttagcaaga   1680
gcagtataca agatgctga tttgtattta ttagactctc cttttggata cctagatgtt   1740
ttaacagaaa agaaatatt tgaaagctgt gtctgtaaac tgatggctaa caaaactagg   1800
attttggtca cttctaaaat ggaacattta aagaaagctg acaaaatatt aattttgcat   1860
gaaggtagca gctatttta tgggacattt tcagaactcc aaaatctaca gccagctttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tatacgaaaa ttttccattg tgcaaaagac tcccttacaa   2160
atgaatggca tcgaagagga ttctgatgag cctttagaga aaggctgtc cttagtacca   2220
gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacataccttt cgatatatta ctgtccacaa gagcttaatt   2580
tttgtgctaa tttggtgctt agtaatttttt ctggcagagg tggctgcttc tttggttgtg   2640
ctgtggctcc ttggaaacac tcctcttcaa gacaaaggga atagtactca tagtagaaat   2700
aacagctatg cagtgattat caccagcacc agttcgtatt atgtgtttta catttacgtg   2760
ggagtagccg acactttgct tgctatggga ttcttcagag tctaccact ggtgcatact   2820
ctaatcacag tgtcgaaaat tttacaccac aaaatgttac attctgttct tcaagcacct   2880
atgtcaaccc tcaacacgtt gaaagcaggt gggattctta atagattctc caaagatata   2940
gcaattttgg atgaccttct gcctcttacc atatttgact tcatccagtt gttattaatt   3000
gtgattggag ctatagcagt tgtcgcagtt ttacaaccct acatctttgt tgcaacagtg   3060
```

```
ccagtgatag tggctttat tatgttgaga gcatatttcc tccaaacctc acagcaactc   3120
aaacaactgg aatctgaagg caggagtcca atttcactc atcttgttac aagcttaaaa   3180
ggactatgga cacttcgtgc cttcggacgg cagccttact ttgaaactct gttccacaaa   3240
gctctgaatt tacatactgc caactggttc ttgtacctgt caacactgcg ctggttccaa   3300
atgagaatag aaatgatttt tgtcatcttc ttcattgctg ttaccttcat ttccatttta   3360
acaacaggag aaggagaagg aagagttggt attatcctga cttagccat gaatatcatg   3420 agtacattgc agtgggctgt aaactccagc atagatgtgg atagcttgat gcgatctgtg   3480
agccgagtct ttaagttcat tgacatgcca acagaaggta aacctaccaa gtcaaccaaa   3540
ccatacaaga atggccaact ctcgaaagtt atgattattg agaattcaca cgtgaagaaa   3600
gatgacatct ggccctcagg gggccaaatg actgtcaaag atctcacagc aaaatacaca   3660
gaaggtggaa atgccatatt agagaacatt tccttctcaa taagtcctgg ccagagggtg   3720
ggcctcttgg gaagaactgg atcagggaag agtactttgt tatcagcttt tttgagacta   3780
ctgaacactg aaggagaaat ccagatcgat ggtgtgtctt gggattcaat aactttgcaa   3840
cagtggagga aagcctttgg agtgatacca cagaaagtat ttattttttc tggaacattt   3900
agaaaaaact tggatcccta tgaacagtgg agtgatcaag aaatatggaa agttgcagat   3960
gaggttgggc tcagatctgt gatagaacag tttcctggga agcttgactt tgtccttgtg   4020
gatgggggct gtgtcctaag ccatggccac aagcagttga tgtgcttggc tagatctgtt   4080
ctcagtaagg cgaagatctt gctgcttgat gaacccagtg ctcatttgga tccagtaaca   4140
taccaaataa ttagaagaac tctaaaacaa gcatttgctg attgcacagt aattctctgt   4200
gaacacagga tagaagcaat gctggaatgc caacaatttt tggtcataga agagaacaaa   4260
gtgcggcagt acgattccat ccagaaactg ctgaacgaga ggagcctctt ccggcaagcc   4320
atcagcccct ccgacagggt gaagctcttt ccccaccgga actcaagcaa gtgcaagtct   4380
aagccccaga ttgctgctct gaaagaggag acagaagaag aggtgcaaga tacaaggctt   4440
tagatgcaga ggtcgcctct ggaaaaggcc agcgttgtct ccaaacttt tttcagctgg   4500 accagaccaa ttttgaggaa aggatacaga cagcgcctgg aattgtcaga catataccaa   4560
atcccttctg ttgattctgc tgacaatcta tctgaaaaat tggaaagaga atgggataga   4620
gagctggctt caaagaaaaa tcctaaactc attaatgccc ttcggcgatg ttttttctgg   4680
agatttatgt tctatggaat cttttatat ttaggggaag tcaccaaagc agtacagcct   4740
ctcttactgg gaagaatcat agcttcctat gacccggata caaggagga acgctctatc   4800 gcgatttatc taggcatagg cttatgcctt ctctttattg tgaggacact gctcctacac   4860
ccagccattt ttggccttca tcacattgga atgcagatga aatagctat gtttagtttg   4920 atttataaga agactttaaa gctgtcaagc cgtgttctag ataaaataag tattggacaa   4980
cttgttagtc tcctttccaa caacctgaac aaatttgatg aaggacttgc attggcacat   5040
ttcgtgtgga tcgctccttt gcaagtggca ctcctcatgg ggctaatctg ggagttgtta   5100
caggcgtctg ccttctgtgg acttggtttc ctgatagtcc ttgccctttt tcaggctggg   5160
ctagggagaa tgatgatgaa gtacagagat cagagagctg ggaagatcag tgaaagactt   5220
gtgattacct cagaaatgat tgaaaatatc caatctgtta aggcatactg ctgggaagaa   5280
gcaatggaaa aaatgattga aaacttaaga caaacagaac tgaaactgac tcggaaggca   5340
gcctatgtga gatacttcaa tagctcagcc ttcttcttct cagggttctt tgtggtgttt   5400
```

```
ttatctgtgc ttccctatgc actaatcaaa ggaatcatcc tccggaaaat attcaccacc    5460
atctcattct gcattgttct gcgcatggcg gtcactcggc aatttccctg ggctgtacaa    5520
acatggtatg actctcttgg agcaataaac aaaatacagg atttcttaca aaagcaagaa    5580
tataagacat tggaatataa cttaacgact acagaagtag tgatggagaa tgtaacagcc    5640
ttctgggagg agggatttgg ggaattattt gagaaagcaa aacaaaacaa taacaataga    5700
aaaacttcta atggtgatga cagcctcttc ttcagtaatt tctcacttct tggtactcct    5760
gtcctgaaag atattaattt caagatagaa agaggacagt tgttggcggt tgctggatcc    5820
actggagcag gcaagacttc acttctaatg tgattatgg gagaactgga gccttcagag    5880
ggtaaaatta agcacagtgg aagaatttca ttctgttctc agttttcctg gattatgcct    5940
ggcaccatta agaaaatat catctttggt gtttcctatg atgaatatag atacagaagc    6000
gtcatcaaag catgccaact agaagaggac atctccaagt ttgcagagaa agacaatata    6060
gttcttggag aaggtggaat cacactgagt ggaggtcaac gagcaagaat ttctttagca    6120
agagcagtat acaaagatgc tgatttgtat ttattagact ctccttttgg atacctagat    6180
gttttaacag aaaaagaaat atttgaaagc tgtgtctgta aactgatggc taacaaaact    6240
aggattttgg tcacttctaa aatggaacat ttaaagaaag ctgacaaaat attaattttg    6300
catgaaggta gcagctattt ttatgggaca ttttcagaac tccaaaatct acagccagac    6360
tttagctcaa aactcatggg atgtgattct ttcgaccaat ttagtgcaga agaagaaat    6420 tcaatcctaa ctgagacctt acaccgtttc tcattagaag gagatgctcc tgtctcctgg    6480
acagaaacaa aaaacaatc ttttaaacag actggagagt ttggggaaaa aaggaagaat    6540
tctattctca atccaatcaa ctctatacga aaatttcca ttgtgcaaaa gactccctta    6600
caaatgaatg gcatcgaaga ggattctgat gagcctttag agagaaggct gtccttagta    6660
ccagattctg agcagggaga ggcgatactg cctcgcatca gcgtgatcag cactggcccc    6720
acgcttcagg cacgaaggag gcagtctgtc ctgaacctga tgacacactc agttaaccaa    6780
ggtcagaaca ttcaccgaaa gacaacagca tccacacgaa aagtgtcact ggcccctcag    6840
gcaaacttga ctgaactgga tatatattca agaaggttat ctcaagaaac tggcttggaa    6900
ataagtgaag aaattaacga agaagactta aaggagtgct tttttgatga tatggagagc    6960
ataccagcag tgactacatg gaacacatac cttcgatata ttactgtcca caagagctta    7020 attttttgtgc taatttggtg cttagtaatt tttctggcag aggtggctgc ttctttggtt    7080
gtgctgtggc tccttggaaa cactcctctt caagacaaag ggaatagtac tcatagtaga    7140
aataacagct atgcagtgat tatcaccagc accagttcgt attatgtgtt ttacatttac    7200
gtgggagtag ccgacacttt gcttgctatg ggattcttca gaggtctacc actggtgcat    7260
actctaatca cagtgtcgaa aattttacac cacaaaatgt tacattctgt tcttcaagca    7320
cctatgtcaa ccctcaacac gttgaaagca ggtgggattc ttaatagatt ctccaaagat    7380
atagcaattt tggatgacct tctgcctctt accatatttg acttcatcca gttgttatta    7440
attgtgattg gagctatagc agttgtcgca gttttacaac cctacatctt gttgcaaca    7500 gtgccagtga tagtggcttt tattatgttg agagcatatt tcctccaaac ctcacagcaa    7560
ctcaaacaac tggaatctga aggcaggagt ccaattttca ctcatcttgt tacaagctta    7620
aaaggactat ggacacttcg tgccttcgga cggcagcctt actttgaaac tctgttccac    7680
aaagctctga atttacatac tgccaactgg ttccttgtacc tgtcaacact gcgctggttc    7740
caaatgagaa tagaaatgat ttttgtcatc ttcttcattg ctgttacctt catttccatt    7800
```

```
ttaacaacag gagaaggaga aggaagagtt ggtattatcc tgactttagc catgaatatc   7860
atgagtacat tgcagtgggc tgtaaactcc agcatagatg tggatagctt gatgcgatct   7920
gtgagccgag tctttaagtt cattgacatg ccaacagaag gtaaacctac caagtcaacc   7980
aaaccataca agaatggcca actctcgaaa gttatgatta ttgagaattc acacgtgaag   8040
aaagatgaca tctggccctc aggggggccaa atgactgtca agatctcac agcaaaatac   8100 acagaaggtg gaaatgccat attagagaac atttccttct caataagtcc tggccagagg   8160
gtgggcctct tgggaagaac tggatcaggg aagagtactt tgttatcagc tttttttgaga  8220 ctactgaaca ctgaaggaga aatccagatc gatggtgtgt cttgggattc aataactttg   8280
caacagtgga ggaaagcctt tggagtgata ccacagaaag tatttatttt ttctggaaca   8340
tttagaaaaa acttggatcc ctatgaacag tggagtgatc aagaaatatg gaaagttgca   8400
gatgaggttg ggctcagatc tgtgatagaa cagtttcctg ggaagcttga ctttgtcctt   8460
gtggatgggg gctgtgtcct aagccatggc cacaagcagt tgatgtgctt ggctagatct   8520
gttctcagta aggcgaagat cttgctgctt gatgaaccca gtgctcattt ggatccagta   8580
acataccaaa taattagaag aactctaaaa caagcatttg ctgattgcac agtaattctc   8640
tgtgaacaca ggatagaagc aatgctggaa tgccaacaat ttttggtcat agaagagaac   8700
aaagtgcggc agtacgattc catccagaaa ctgctgaacg agaggagcct cttccggcaa   8760
gccatcagcc cctccgacag ggtgaagctc tttccccacc ggaactcaag caagtgcaag   8820
tctaagcccc agattgctgc tctgaaagag gagacagaag aagaggtgca agatacaagg   8880
ctttag                                                             8886
```

```
<210> SEQ ID NO 7
<211> LENGTH: 8
<212> TYPE: PRT
<213> ORGANISM: Artificial Sequence
<220> FEATURE:
<223> OTHER INFORMATION: DOMAIN Amino Acids 1-8 (entire sequence) =
      antigenic epitope
      commonly known as FLAG tag

<400> SEQUENCE: 7

Asp Tyr Lys Asp Asp Asp Asp Lys
1               5

<210> SEQ ID NO 8
<211> LENGTH: 55
<212> TYPE: DNA
<213> ORGANISM: Artificial Sequence
<220> FEATURE:
<223> OTHER INFORMATION: Oligo-Box B RNA that contained sequence
      complimentary to CFTR nt 1454-1465 and 1469-1491.

<400> SEQUENCE: 8
taatctagga aaactgagaa cagaggccct gaaaaagggc caaattcttc caccc          55
```

SITE-DIRECTED RNA EDITING

FEDERAL GRANTS

This research was supported, in part by the National Institute of Health (NIH) through their NS039405-06 grant. The Government has certain rights in this invention.

SEQUENCE LISTING

The sequence listing submitted via EFS, in compliance with 37 CFR §1.52(e) (5), is incorporated herein by reference. The sequence listing text file submitted via EFS contains the file "UPR-11185_ST25.txt", created on Jul. 13, 2016, which is 24,465 bytes in size.

BACKGROUND OF THE INVENTION

RNA editing by adenosine deamination is believed to occur in most metazoans. It is catalyzed by the ADAR (Adenosine Deaminases that Act on RNA) family of enzymes, which convert adenosine to inosine. During translation inosine is read as guanosine, and therefore this mechanism can change codons in mRNAs. These changes can affect protein structure and function. Any codon change which requires the conversion of adenosine to guanosine is possible. ADARs are composed of a c-terminal catalytic domain that carries out the deamination reaction and two to three double-stranded RNA binding domains (dsRBDs) that bind to the substrate RNA. The dsRBDs are the natural targeting mechanism for ADARs. In natural systems, specific adenosines are selected for editing based on the dsRBDs' ability to recognize secondary and tertiary structure within the surrounding RNA. Often the necessary higher order structures are complex. Our goal is to be able to target ADARs to a selected adenosine. The natural targeting mechanism of ADARs, namely the dsRBDs, would not serve this purpose because they require a specific higher order RNA structure in cis. The probability that such a structure exists around a specific selected adenosine is very low.

SUMMARY OF THE INVENTION

The present invention replaces the natural targeting mechanism of ADARs, the dsRBDs, with an antisense RNA oligonucleotide. An antisense RNA oligonucleotide has the advantage that it can be synthesized to specifically bind to any region of RNA through Watson-Crick base-pairing. Thus by coupling different oligonucleotides to ADAR's deaminase domain, we can guide the domain to different regions of RNAs for specific editing. The deaminase domain is couple to the antisense oligonucleotide by taking advantage of a small RNA binding protein (1N peptide) and the RNA hairpin that it recognizes (boxB hairpin). The (1N peptide is fused to the N-terminus of the deaminase domain of ADAR and the boxB RNA hairpin is inserted into the antisense guide RNA.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
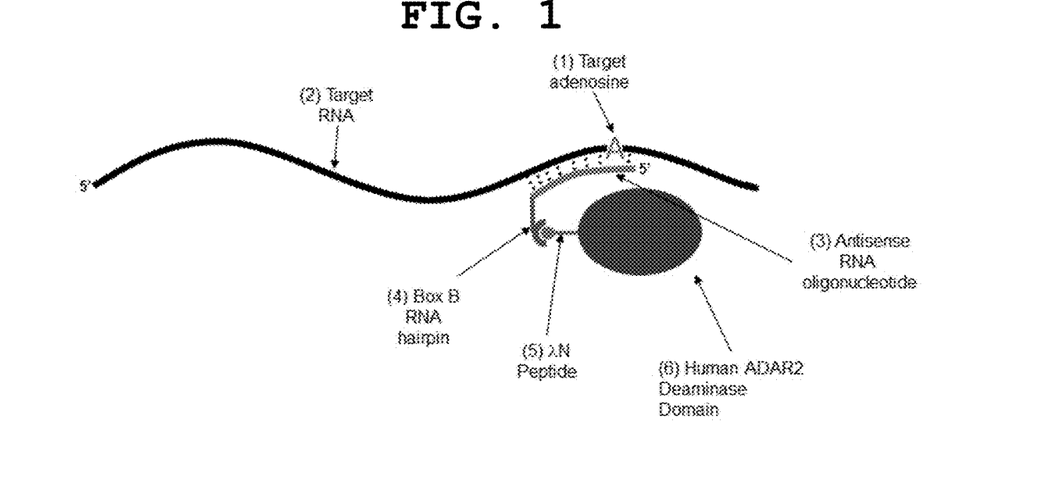
FIG. 1 illustrates the site-directed RNA editase method according to the present invention.

The present invention provides a site-directed RNA editase. It is composed of a protein to carry out the adenosine deamination and an antisense RNA oligo to guide the protein to the correct location. The method of the present invention is illustrated in FIG. 1. A critical aspect of this novel method is how to attach the antisense RNA oligonucleotide, used as a guide, to the deaminase domain of ADAR, to be used to catalyze the editing reaction. For this purpose we used the bacteriophage λ N-peptide RNA binding protein (SEQ ID:3) and the Box B RNA hairpin loop (SEQ ID:2), its natural interaction partner (Chattopadhyay et al., 1995a. Tan & Frankel, 1995). Now the inventive method will be explained in relation to FIG. 1. The first element is an adenosine we wish to target 1 within a RNA molecule 2. This can be any adenosine within any RNA. The second element is an antisense RNA oligonucleotide 3. The 5' end of the oligonucleotide should begin before (on the 3' side) of the target adenosine. The 3' end of the oligonucleotide should extend up to 21 nucleotides 5' from the target adenosine. On the 3' end of the oligo we have fused the Box B RNA sequence 4 (SEQ ID:2). The bacteriophage λ N-peptide 5 (SEQ ID:3) binds to the Box B RNA sequence 4 (SEQ ID:2). Fused to the C-terminus of the bacteriophage λ N-peptide 5 (SEQ ID:3) is the deaminase domain of human ADAR2 6 (SEQ ID:1). Thus, the antisense RNA oligonucleotide is used for targeting the entire complex to a specific address on the RNA molecule. The Box B RNA (SEQ ID:2) and the λ N-peptide (SEQ ID:3) are used as a linkage between the antisense RNA oligonucleotide and the deaminase domain of human ADAR2 (SEQ ID:1). The deaminase domain of human ADAR2 is used to catalyze the deamination of the specific adenosine residue. These elements make up two molecules: the antisense RNA oligonucleotide-Box B RNA hairpin forms a single unit (referred to hereafter as Oligo-Box B), as does the λ N-peptide-deaminase domain of human ADAR2 (referred to hereafter as λN-DD).

Production of Oligo-Box B and λN-DD

Figure 2:
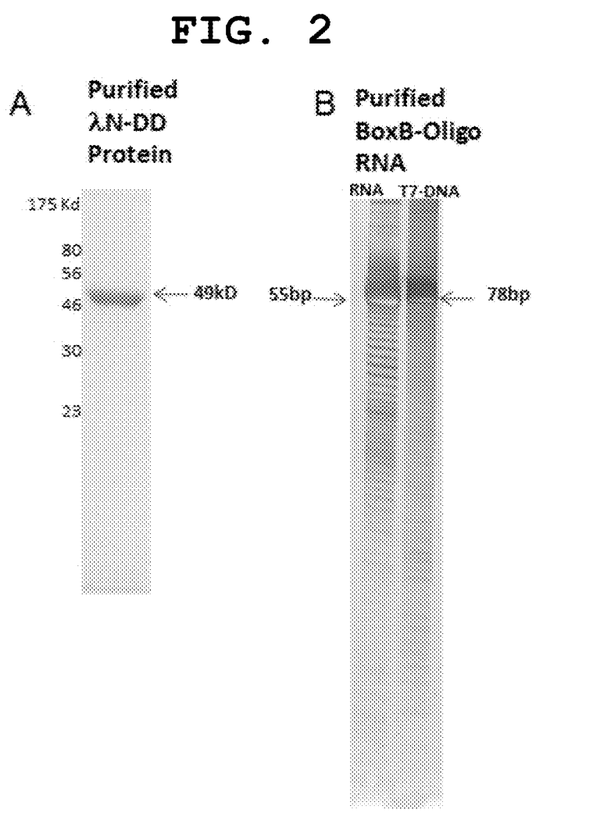
FIG. 2 shows the purified λN-DD in panel A and the purified RNA Oligo-Box B in panel B according to the present invention.

The primary aim of the invention was to synthesize both Oligo-Box B and λN-DD. Oligo-Box B was made by buying a DNA oligonucleotide encoding a T7 RNA polymerase promoter at the 5' end followed by the Oligo-Box B sequence. The "oligo" sequence corresponds to a variable length of antisense sequence, complementary to the RNA that is being targeted. The BoxB sequence (SEQ ID:2) is given in the previous section. An antisense version of the same DNA oligonucleotide was also synthesized. The two were then hybridized together and used as a template to make RNA with T7 RNA polymerase. λN-DD was made by cloning the encoding DNA sequence (all available on the public nucleotide database at www.ncbi.nih.gov) into the pPICZ A vector purchased from Invitrogen (Carlsbad, Calif.) and including an N-Terminal FLAG epitope tag (DYKDDDDK) (SEQ ID:7) and six histidines at the C-terminus. The protein was then expressed in the yeast *Pichia pastoris* (strain GS115 from Invitrogen, Carlsbad, Calif.) and purfied first over a Ni-Nitriloacetic Acid column followed by an Anti-FLAG affinity column. FIG. 2 shows the purified λN-DD in panel A and the purified RNA Oligo-Box B in panel B. In this case, the "oligo" part of the sequence is complimentary to nt 1454-1465 and 1469-1491 of CFTR (NCBI reference sequence NM_000492.3).

Evidence that Oligo-Box B and λN-DD are Active

Figure 3:
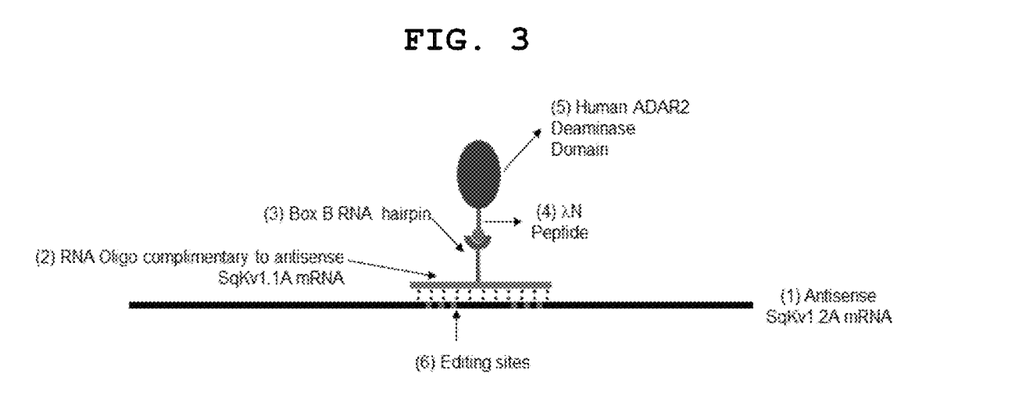
FIG. 3 illustrates the method using Oligo-Box B and λN-DD to specifically edit RNA encoding the squid K+ channel SqKv1.2A according to the present invention.

We first tested Oligo-Box B and λN-DD's ability to specifically edit RNA encoding the squid K⁺ channel SqKv1.2A as illustrated in FIG. 3. For this experiment, Oligo-Box B complex was slightly different than the one previously described. The sequence length of the entire oligonucleotide was: 131 bp. The antisense portion of the oligonucleotide (SEQ ID:4) was complimentary to nucleotides 501-613 of SqKv1.2A. The Box B loop was inserted in the middle of the oligo, between nucleotides that are complimentary to positions 554 and 555 of SqKv1.2A. Note that this step is different than the one described previously, where the Box B loop was positioned at the 5' end of the oligo. In our experiments, we vary the position of the BoxB loop and still have a functional interaction. This Oligo-Box B, was combined with λN-DD protein and SqKv1.2A RNA in vitro. After incubation, the SqKv1.2A RNA was converted into cDNA. Direct sequencing of RT-PCR products showed editing at nucleotides 530, 536, 537, 544, 547, 553, 568, 573, 574, 575, 580, 581, 584, 585 and 607. All of these positions were under the antisense oligo and adjacent to the Box B loop. Control experiments that lacked either the Oligo-Box B or the λN-DD protein showed no editing. In similar experiments, we showed that by adding excess of commercially synthesized Box B oligo sequence or λN peptide could block the reaction. Taken together, these data show the Box-B-λN interaction is required to target the catalytic domain of ADAR to the edited positions. These experiments show that editing was particularly active at positions 573, 574 and 575. These positions are centered 19, 20 and 21 nucleotides on the 5' side of the Box B attachment.

Figure 4:
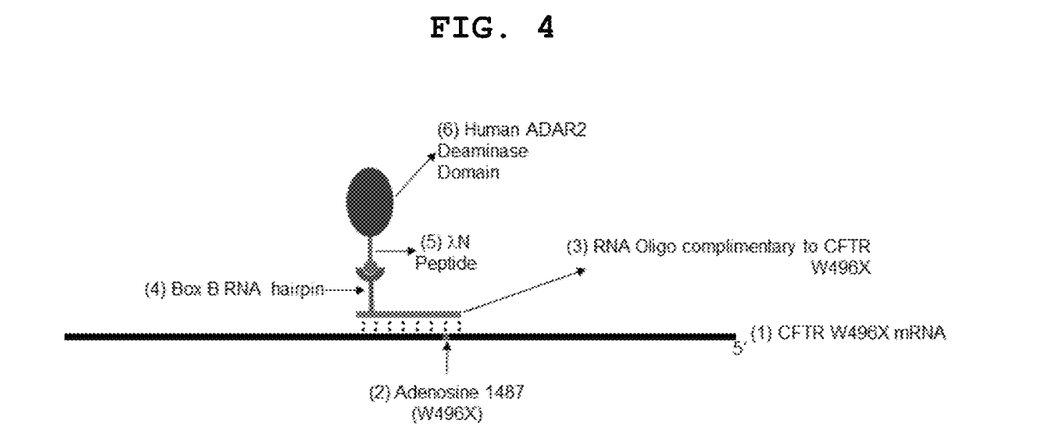
FIG. 4 illustrates the method using the Oligo-Box B and λN-DD's to correct a premature termination codon within CFTR according to the present invention.

Based on the above results, we tested whether we could use this system to correct a genetic mutation in vitro as illustrated in FIG. 4. We targeted nt 1487 in human cystic fibrosis transmembrane conductance regulator (CFTR) mRNAs, messages which encode a protein involved in the transport of chloride ions across cell membranes. In wild type CFTR, this position is encoded by a guanine. Some people carry a mutant CFTR where this position has been mutated to Adenosine (Balassopoulou et al., 1994). This mutation changes codon 496 from a tryptophan residue to a premature termination codon (PTC). Thus people with two copies of the W496X mutation make truncated, non-functional CFTR proteins and often develop the disease Cystic Fibrosis. Using our approach, we have corrected the W496X mutation back to W (tryptophan) by editing Adenosine 1487 to inosine. From the experiments previously described, we learned that when guided by an antisense oligo, the λN-DD protein will edit at a position 20 nt 5' of the position of the Box B loop insertion. Accordingly, we made an Oligo-Box B RNA that contained sequence complimentary to CFTR nt 1454-1465 and 1469-1491. The entire sequence of this construct was (SEQ ID: 8)
(TAATCTAGGAAAACTGAGAACAGAGGCCCTGAAAAAGGGCCAAATTCTT

CCACCC).

The first two nucleotides were added to optimize the transcriptional efficiency of the oligo. When this RNA was combined with λN-DD protein and CFTR W496X (SEQ ID:5) in vitro, we were able to correct approximately 97% of the mutant CFTR RNA, changing nt 1487 to inosine and thus correcting codon 496 back to W. Editing was specific to this adenosine.

Figure 5:
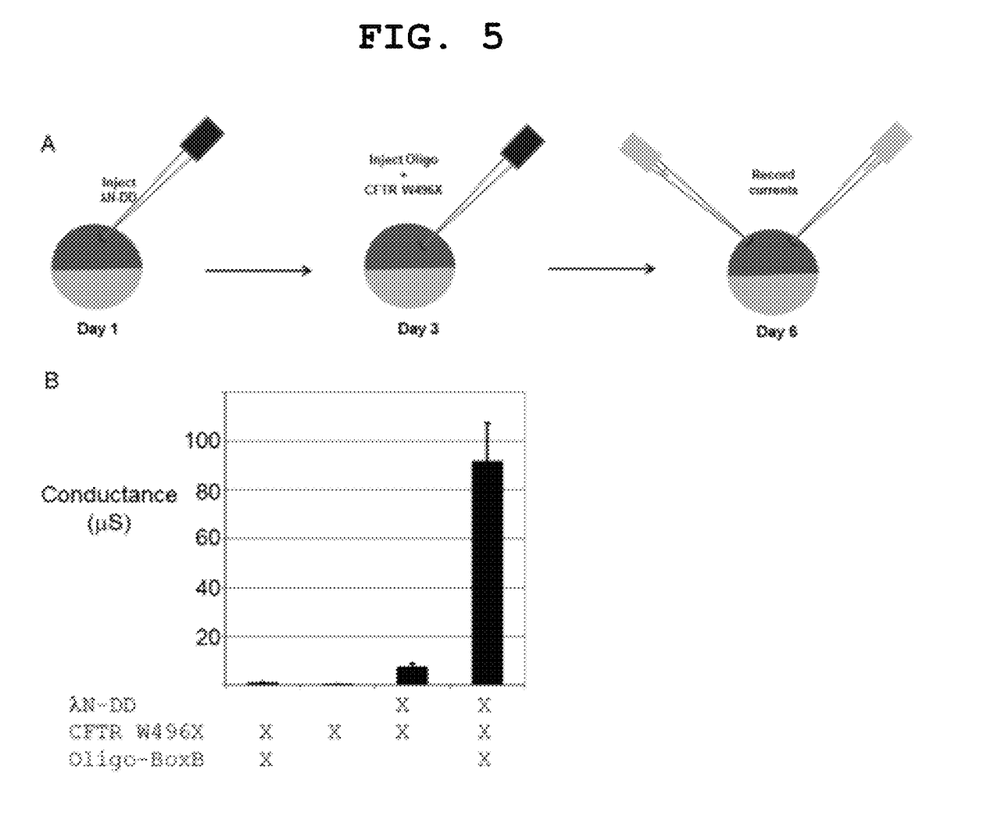
FIG. 5 illustrates the method for correcting CFTR W496X in *Xenopus* oocytes according to the present invention.

We have also tested our strategy in living cells. When *Xenopus* oocytes are injected with mRNA for wild type CFTR (SEQ ID:6), they produce functional chloride channels whose currents can be monitored by standard voltage clamp techniques. CFTR channels open in response to ATP and cyclic AMP. ATP levels within an oocyte are sufficient to open the channels, but cyclic AMP levels must be increased by exposing the oocytes to Forskolin. After about 1 day, *Xenopus* oocytes injected with wt CFTR produce large currents when activated with 40 μM external Forskolin. Oocytes injected with CFTR carrying the W496X mutation express no current over background for at least 7 days. FIG. 5 illustrates an experiment designed to correct CFTR W496X. We injected oocytes with RNA encoding λN-DD. Three days later we injected them again with Oligo-BoxB RNA and RNA encoding CFTR W496X. After three more days total membrane conductance was measured under voltage clamp. Experimental oocytes produced large conductances (>80 mS) when exposed to 40 μM external Forskolin. Oocytes that lacked the Oligo Box B RNA or the λN-DD RNA, or oocytes that were injected with only CFTR W496X, produced no current over background. These results indicated that we could successfully correct a genetic mutation and restore a portion of CFTR function within a living cell. In principle, this strategy should work equivalently with other PTCs.

The ability to change genetic information at the level of RNA has many practical applications. We envision that Oligo Box B and λN-DD could be delivered to cells in order to correct genetic mutations that result in premature termination codons (UAG, UAA, UGA). In some cases, the wt codon is a tryptophan (UGG). In these cases, editing would restore function. Sometimes the wt codon is for a different amino acid. We anticipate that in some cases protein function would support a tryptophan at these positions and thus our strategy could restore a portion of protein function. The Oligo Box B could be delivered as DNA, which would be transcribed into RNA, or as RNA. The λN-DD could be delivered as DNA, RNA or protein. Oligo Box B and λN-DD could also be delivered to cells in order to correct stop codon mutations and missense mutations that can be corrected by changing A to G. Oligo Box B and λN-DD could also be delivered to cells in order to introduce compensatory mutations to counteract genetic mutations that cause a specific deficit in protein function. Oligo Box B and λN-DD could also be delivered to cells in order to improve protein function. In addition, it can be used to develop strains of model organisms, including but not limited to rats, mice or *Drosophila melanogaster*, that express Oligo Box B RNA and λN-DD protein. These engineered organisms could then serve as models for specific human diseases by introducing the correct mutations.

The basic concept behind the present invention is to guide an RNA editing enzyme to a specific residue within a mRNA by coupling it to an antisense oligonucleotide. There are many alternative approaches that could be effective. Besides human ADAR2, different ADAR catalytic domains could be used. They may have different preferences for adenosines depending on the context of the surrounding nucleotides and this could improve editing efficiency. Besides using the catalytic domain from an adenosine deaminase, the catalytic domain of a cytidine deaminase could be used to make C to U conversions in RNA. In addition, the full-length cytidine deaminase could be used. Besides using the catalytic domain from an adenosine deaminase, the catalytic domain of a cytidine deaminase like Activation-induced cytidine deaminase (AID) or APOBEC1 could be used to make C to U conversions in DNA. Further improvements to site-directed editors could be made by introducing mutations in the catalytic domain of ADAR or a cytidine deaminase could be added to alter selectivity, specificity or to modify catalytic activity. Antisense oligonucleotides could be linked at locations other than the N-terminus in order to alter selectivity of specificity. The sequence or the length of the linkage between the λN peptide and the ADAR2 deaminase domain could be modified in order to 1) regulate the distance that editing occurs away from the location of the BoxB loop or 2) the flexibility of the linkage with the idea that a more rigid structure would increase the specificity of editing site selection.

Different linkages between the catalytic domain of ADAR and the antisense oligo could be used. In a preferred embodiment of the invention, BoxB RNA and λN RNA binding peptide are used to create the linkage. Alternatively, a direct covalent linkage between the catalytic domain of ADAR and the antisense oligo could be used. In addition, different RNA-RNA binding protein could be used. Modifications to the antisense oligonucleotide structure could be made in order to stabilize it, prevent it from being degraded, to regulate its affinity for its target, to increase its catalytic efficiency, or to decrease the extent to which it blocks translation. Chemical modifications to the nucleosides could be introduced to either the bases or the sugars. Deoxynucleotides could be used instead of ribonucleosides.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A method of editing a nucleotide within a RNA molecule comprising:
   identifying an adenosine within said RNA molecule;
   binding an antisense RNA oligonucleotide to a region surrounding said adenosine; and
   providing a human ADAR2 deaminase domain (SEQ ID:1) linked to said antisense RNA oligonucleotide.

2. The method of claim 1, comprising a 5' end of the antisense RNA oligonucleotide beginning before said adenosine on a 3' end, wherein a 3' end of the antisense RNA oligonucleotide extends up to 21 nucleotides 5' from said adenosine.

3. The method of claim 1, wherein a Box B RNA (SEQ ID:2) and a λ N-peptide (SEQ ID:3) are used as a linkage between said antisense RNA oligonucleotide and said deaminase domain of human ADAR2 (SEQ ID:1).

4. The method of claim 1, wherein said human ADAR2 deaminase domain (SEQ ID:1) is linked to said antisense RNA oligonucleotide by: fusing a Box B RNA sequence (SEQ ID:2) on the 3' end of said antisense RNA oligonucleotide; binding a bacteriophage λ N-peptide (SEQ ID:3) to said Box B RNA sequence (SEQ ID:2); and fusing the deaminase domain of human ADAR2 (SEQ ID:1) to a C-terminus of said bacteriophage λ N-peptide (SEQ ID:3).

5. The method of claim 1, wherein the deaminase domain of human ADAR2 (SEQ ID:1) is used to catalyze the deamination of a specific adenosine residue.

* * * * *

UNITED STATES PATENT AND TRADEMARK OFFICE
CERTIFICATE OF CORRECTION

PATENT NO. : 9,650,627 B1
APPLICATION NO. : 13/947027
DATED : May 16, 2017
INVENTOR(S) : Joshua J. C. Rosenthal and Maria Fernanda Montiel-Gonzalez It is certified that error appears in the above-identified patent and that said Letters Patent is hereby corrected as shown below:

In the Specification

Column 1, Lines 3-7 should read:
GOVERNMENT INTEREST
This invention was made with government support under grant NS039405 awarded by the National Institute of Health (NIH). The Government has certain rights in this invention.

Signed and Sealed this
Twelfth Day of March, 2019

Andrei Iancu
*Director of the United States Patent and Trademark Office*